United States Patent
Seney

Patent Number: 5,096,421
Date of Patent: Mar. 17, 1992

[54] DENTAL BUR COOLING SYSTEM

[76] Inventor: John S. Seney, Box 152, Sugarloaf Key, Fla. 33044

[21] Appl. No.: 472,072

[22] Filed: Jan. 30, 1990

Related U.S. Application Data

[63] Continuation-in-part of Ser. No. 421,659, Oct. 16, 1989, abandoned.

[51] Int. Cl.$^5$ .............................................. A61C 1/12
[52] U.S. Cl. ........................................ 433/82; 433/84; 433/165
[58] Field of Search ............... 433/82, 83, 84, 85, 433/165, 166

[56] References Cited

U.S. PATENT DOCUMENTS

| | | | |
|---|---|---|---|
| 1,361,335 | 12/1920 | Kampe | 433/129 |
| 2,777,702 | 1/1957 | Rodal | 408/59 |
| 2,799,934 | 7/1957 | Kern | 433/104 |
| 3,534,476 | 10/1970 | Winters | 433/165 |
| 3,624,905 | 12/1971 | Barsby | 433/82 |
| 3,762,052 | 10/1973 | Melde | 433/165 |
| 3,871,097 | 3/1975 | Melde | 433/82 |
| 4,021,920 | 5/1977 | Kirschner et al. | 433/165 |

*Primary Examiner*—John J. Wilson

[57] ABSTRACT

An air-turbine type dental handpiece in which the handle has separate passages for air and water under pressure respectively to drive the turbine to rotate a bur and furnish cooling water to the bur which has an axial passage entirely therethrough to direct the cooling water where the cutting end of the bur contacts tooth material for producing a dental preparation to receive filling material and the like. The head of the handpiece has a chamber within which the turbine and bearings are mounted and also includes a rotary coupling to direct cooling water to the inner end of the axial passage of said bur and prevents escape of the cooling water to the interior of the chamber for the turbine and bearings. The coupling is bipartite and one of the parts comprises the innermost end of the bur when mounted within the shaft of the turbine. Control mechanism to furnish and regulate the pressure of air and water to the handpiece also comprises part of the invention and an anti-clogging device is included in the passage in the bur.

14 Claims, 5 Drawing Sheets

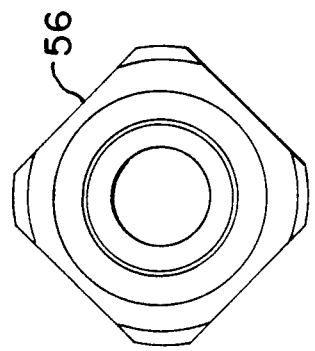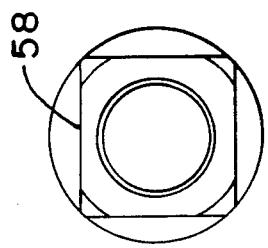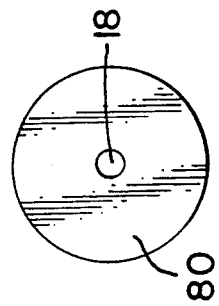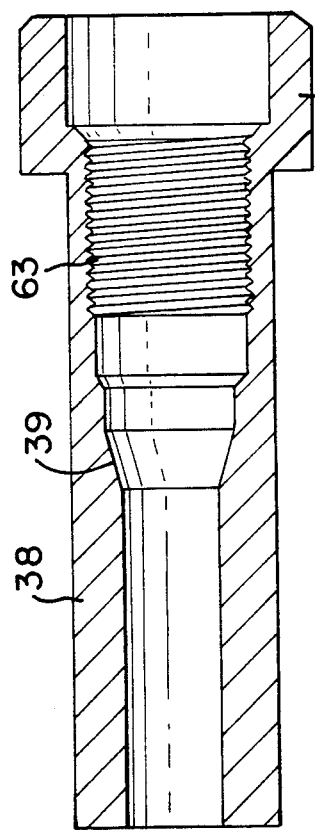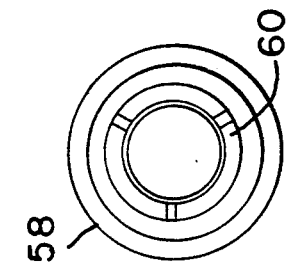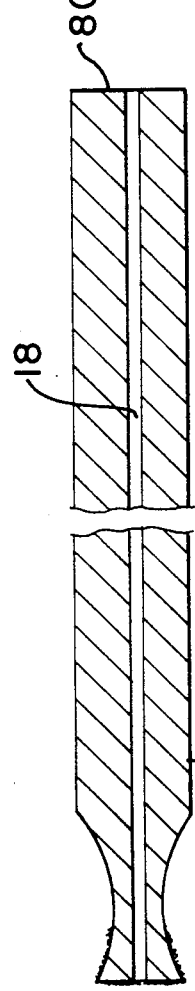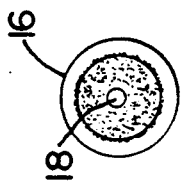

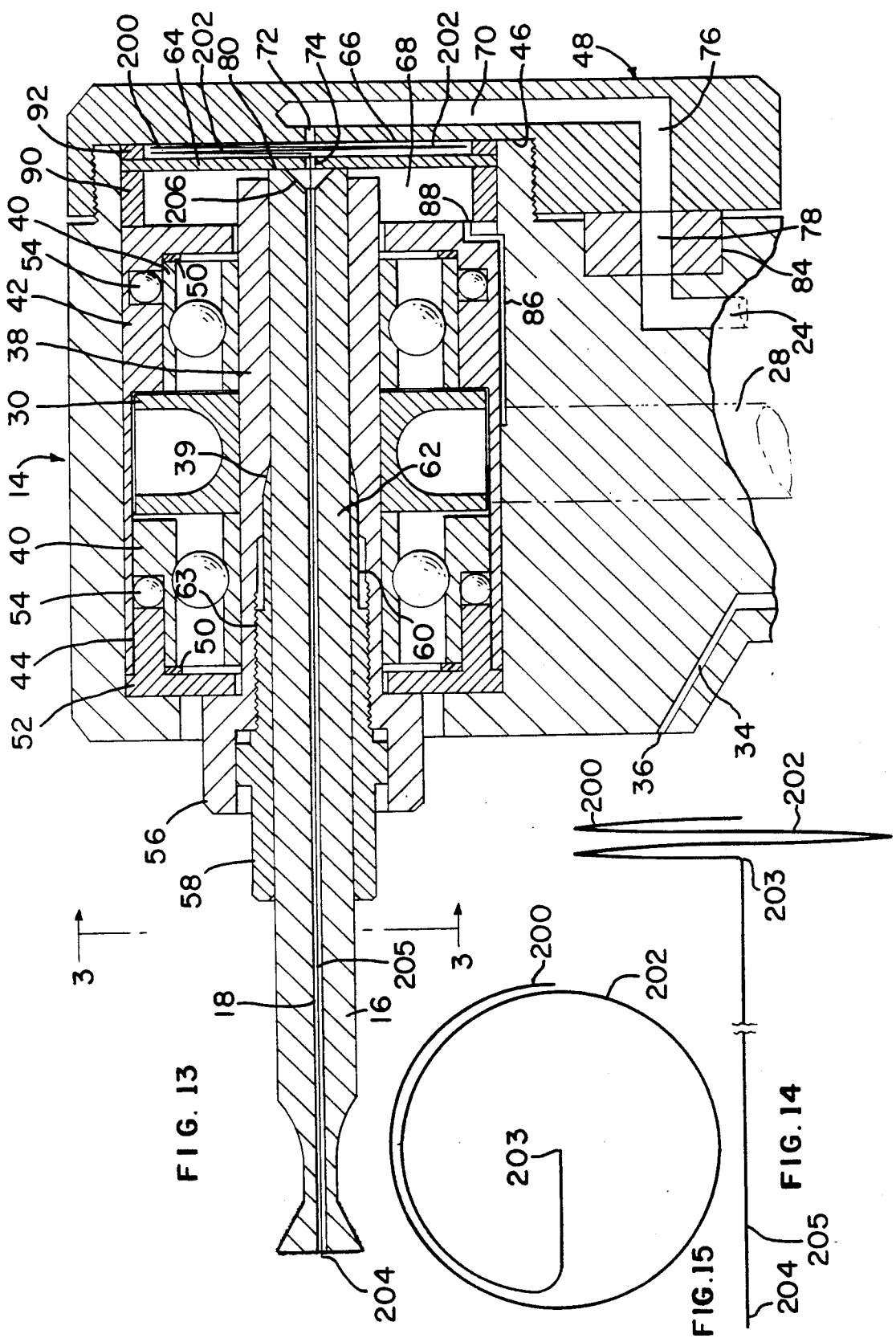

DENTAL BUR COOLING SYSTEM

This application is a continuation-in-part of U.S. Ser. No. 07/421,659, filed Oct. 16, 1989, now abandoned.

BACKGROUND OF THE INVENTION

The preparation of cavities for acceptance of filling material is normally one of the very painful experiences encountered by a patient being subjected to the practice of dentistry. Attempts have previously been made to cool a tooth in which such a preparation is being undertaken by means of a dental assistant spraying water upon the operation, as well as many types of dental handpieces having water jets which operate to direct a stream of water at the area of the tooth where drilling is taking place. None of these systems actually direct cooling fluid such as water into the actual cavity where the cutting is taking place by the bur of the handpiece. Many modern handpieces also operate at very high speeds, as much as 400,000 rpm. Handpieces operating at such speeds require much less pressure than those operating at slower speeds, such as when they are driven by belts and the like.

It has been found by acurate scientific instruments that handpieces operating at such high speeds as mentioned above, involve problems with respect to generating heat in the tooth where the preparation is being formed. Laboratory measurements show a temperature at the bur-tooth interface of 450 degrees F. with a bur pressure of 32 grams at a bur speed of 170,000 rpm, after a running time of 30 seconds. The pulp section of a tooth contains nerves, blood vessels and lymph-carrying vessels, which are destroyed by high temperatures. Fillings placed over such damage can result in infection and abscesses. To alleviate this situation, cooling water jets are built into handpieces with their sprays directed at the cutting bur tip. However, laboratory tests show that little or no water contacts the bur tip per se because of turbulant air surrounding the same. It has been found that a minimum water flow rate of 16 cc/minute is necessary to form a stream with force enough to reach the bur tip area in a commercial 4-hole handpiece. This quantity of water floods the operating area, fogs the dental mirror, and reduces the view of the operating site. Contaminated water mist and sprays exit from the patient's mouth and settle on persons in the general area, creating a serious health hazard, especially when diseases such as AIDS and hepatitis may be present. It has been found that when the bur cuts below the outer surface of the tooth, cooling water entering that area is blocked by the projecting surfaces of the tooth and uncontrolled heating results.

Attempts have previously been made to direct water to the tip of a rotating bur by providing dental burs which have longitudinal passages extending entirely through the bur from one end to the other, but the problems mainly resulting from the use of such burs in dental handpieces reside in difficulties encountered when endeavoring to restrict cooling liquid, such as water, solely through the longitudinal opening in the bur, while in most instances, some of the cooling liquid enters the interior of the head in the vicinity of the turbine, under which circumstances, the lubricant normally required by the bearings of so-called air-rotor handpieces is flushed from the bearings or at least diluted by such water.

It is the principal object of the present invention to provide a dental handpiece which includes means to direct cooling liquid, such as water, through a bur which is provided with a longitudinal passage between opposite ends and discharge the water from the outer end of the bur directly to the interface between the bur and the tooth and improved means are included which are highly adequate to prevent the cooling liquid from reaching and/ or admixing with air turbines and the bearings therefor, details of which are set forth below.

To illustrate the present state of the art in which dental handpieces are provided with burs having axial passages between opposite ends of the bur, and means to direct cooling liquid thereto or therethrough, the following patents are cited as representative of the current state of the art on this subject:

| U.S. Pat. No. 2,777,702 - Rodal | Jan. 15, 1957 |
| U.S. Pat. No. 2,799,934 - Kern | July 23, 1957 |
| U.S. Pat. No. 3,624,905 - Barsby | Dec. 7, 1971 |
| U.S. Pat. No. 3,762,052 - Melde (1) | Oct. 2, 1973 |
| U.S. Pat. No. 3,871,097 - Melde (2) | Mar. 18, 1975 |
| U.S. Pat. No. 4,021,920 - Kirschner | May 10, 1977 |
| U.S. Pat. No. 4,869,668 - Seney | Sept. 26, 1989 |

SUMMARY OF THE INVENTION

The present invention comprises a modification of the invention comprising the subject matter of applicant's prior U.S. Pat. No. 4,869,668, dated Sept. 26, 1989.

It is another principal object of the present invention to provide a dental handpiece for use with a dental bur in which a longitudinal passage extends therethrough between the opposite ends thereof, the head of the handpiece being connected to a handle extending therefrom and provided with longitudinal passages therein for cooling liquid, flushing liquid and air to drive the turbine within the head of the handpiece, the principal feature of the present invention comprising a rotary liquid transmission coupling mounted within the upper portion of the head of the handpiece and extending between the passage in the handle for cooling liquid and upper end of the bur inside the shaft of the turbine, said coupling including sealing means to prevent the leakage or migration of cooling liquid into the interior of the head in which the turbine, and especially the bearings therefor, are enclosed, whereby the normal lubricant for the bearings is not diluted or otherwise affected.

Another object of the present invention, as compared with applicant's prior patent, is to position said rotary transmission coupling in the upper end of the head of the handpiece and comprises a thin flexible diaphragm sealed at its edges between a relatively flat space in the uppermost portion of the head to receive cooling liquid which produces pressure against one surface of said diaphragm and the opposite face of the diaphragm comprising a closure for a small circular space in which the innermost end of the bur surface, per se, directly and rotatably engages said diaphragm and thereby forms a rotary seal member which prevents cooling liquid from contacting the bearings for the turbine, and said small annular space communicates with a bypass through which part of the driving air for the turbine passes to exert limited pressure against one face of the diaphragm while cooling liquid exerts pressure against the opposite face and the pressure and volume of the air and cooling liquid are regulated so that the diaphragm will always contact the innermost end of the bur and said diaphragm has an opening which is coaxial with the innermost end of the axial passage for cooling liquid in the bur and due to such regulation of pressure and volume referred to, a liquid seal is maintained between said rotary seal and diaphragm.

Still another object of the invention, in contrast to applicant's prior patent, is to utilize burs which have the end opposite the cutting end superpolished and absolutely flat for engaging the diaphragm in the head of the bur, whereby the present invention comprises a combination of the end of the bur, such as described above, and the foregoing detail of the bur.

One further object of the invention is to form said diaphragm preferably from a self-lubricating plastic, such as one sold under the trademark "NYLON", and the rotary seal is formed by the rotary engagement of the superpolished flat end of the hollow bur with said plastic diaphragm, whereby minimum friction occurs between said relatively rotating surfaces of the polished end of the bur and the diaphragm, the principal purpose of the air exerting pressure against one surface of the diaphragm is to prevent undue friction between the diaphragm and rotary seal, especially at the start-up of the turbine and until cooling liquid can be exerted against the opposite surface of the diaphragm and discharge through the coaxial openings in the diaphragm and the polished inner end of the bur and thereafter pass through the bur to the outermost end thereof.

A still further object of the invention is to provide control means for the delivery of cooling liquid and air to the head of the handpiece, said substances being conducted in separate conduits respectively including filters, pressure regulators, electric solenoid valves which are respectively connected to sources of current and include lines within which control switches are provided in conjunction with a foot-operated switch, the handle of the handpiece also including a still further longitudinal passage through which flushing water passes from a source through another control switch of electric solenoid nature, the flushing liquid being directed to an exterior nozzle adjacent the head of the handpiece and extending toward the outer end of the bur for purposes of flushing debris from a cavity preparation operation. In addition to the cooling liquid discharging through the tip of the bur at the innerface between the bur and tooth surface to cool the area being cut by the bur and thus afford relative comfort to a patient, the respective control switches in the lines for the cooling and flushing liquids being operable in conjunction with the foot-operated switch to selectively discharge driving air to the turbine, cooling liquid only to the tip of the bur, flushing liquid only to the flushing jet, both cooling liquid to the tip of the bur and flushing liquid to the jet, or flushing liquid to the jet only, thus affording a dentist a range of functions for the several liquids, as well as driving air and air directed against one face of the diaphragm of the rotary liquid transmission coupling.

Still another object of the invention is also to provide additional liquid volume control valves of manually-operable nature respectively in the lines for the cooling liquid and also the flushing liquid directed to the external jet on the head of the handpiece.

One further object of this invention as compared with applicant's prior patent, is to provide a bur modified securing tightening nut having a thin flexible segmented tapered extension on its interior end, that engages a mating tapered bore in the turbine shaft, whereby tightening the tightening nut reduces the bore diameter around the shank of the bur and secures the bur to the turbine shaft and thus preventing any relative rotation between the shank of the bur and said shaft of the turbine.

It now has been found that when drilling certain materials in dental practice, such as bone and non-crystalline tooth materials, that the cutting debris tends to clog the coolant passage in the bur and stops flow of the coolant to the areas in a tooth preparation where cooling is desired. Therefore, it is a still further object of this invention to provide an anti-clogging device, which is partly disposed in the head of the handpiece and partly in the longitudinal passage or bore in the bur, and serves to prevent any tendencies for such debris to accumulate in said passage by constantly being flushed from the passage by the coolant as it passes therethrough.

Details of the foregoing objects and of the invention, as well as other objects thereof, are set forth in the following specification and illustrated in the accompanying drawings comprising a part thereof.

BRIEF DESCRIPTION OF THE DRAWINGS

FIG. 4 is a longitudinal sectional view of applicant's modified turbine shaft having interior constricting means engageable by a modified tightening nut to brace the intermediate portion of the bur.

FIG. 5 is a plan view of the right-hand end of FIG. 4.

FIG. 6 is a longitudinal sectional view of applicant's modified tightening nut having longitudinal slits in the innermost end which are compressible against the intermediate portion of the bur when fully tightened within the hollow turbine shaft.

FIG. 7 is a plan view of the left-hand end of FIG. 6.

FIG. 8 is a plan view of the right-hand end of FIG. 6.

FIG. 9 is a foreshortened longitudinal sectioned view of applicant's bur on which the end opposite the cutting end is superpolished and absolutely flat.

FIG. 10 is a plan view of the left-hand end of FIG. 9.

FIG. 11 is an enlarged plan view of the right-hand end of FIG. 9.

FIG. 13 is another cross-sectional view of the head of the handpiece, similar to FIG. 2, but including an anti-clogging device operable primarily in the longitudinal passage or bore in the bur.

FIG. 14 is a side view of the anti-clogging device, and FIG. 15 is an axial plan view of the anti-clogging device as seen from the upper coiled end thereof.

DETAILED DESCRIPTION OF THE PREFERRED EMBODIMENT OF THE INVENTION

Figure 1:
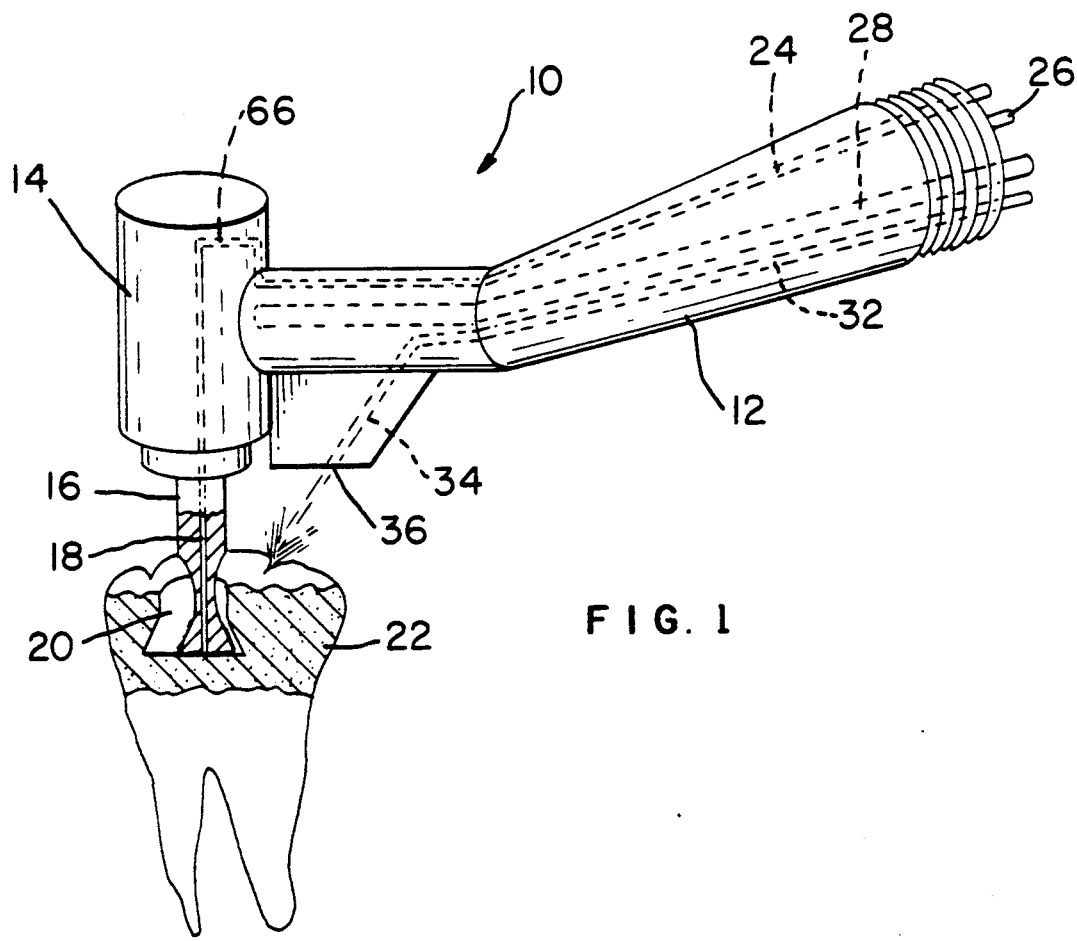
FIG. 1 is a side elevation of a dental handpiece embodying the principles of the present invention and being illustrated in process of preparing a cavity within a tooth, a portion of the tooth being shown in section, to illustrate details of the tip of the bur and said view illustrating in phantom certain passages for liquid and air extending longitudinally through the handle and communicating with the interior of the head of the handpiece.
Figure 3:
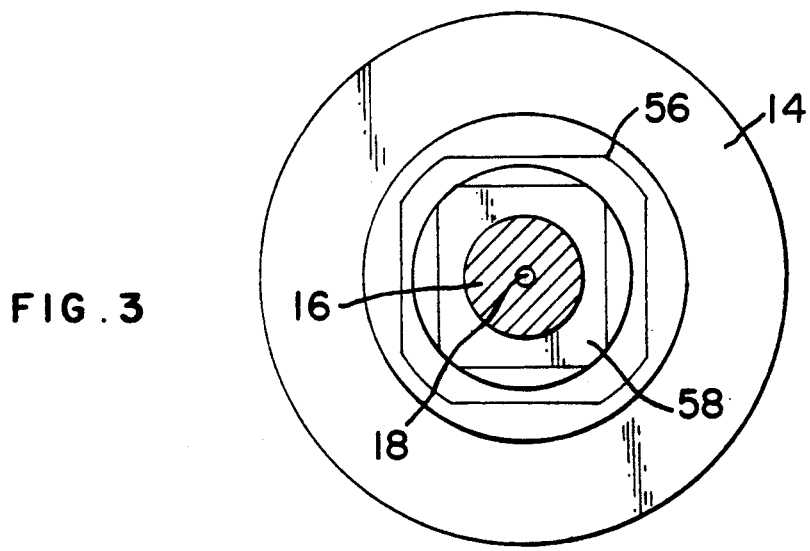
FIG. 3 is an enlarged transverse sectional view as seen on the line 3—3 of FIG. 2.

The present invention primarily relates to a dental handpiece and control mechanism therefor in which a continuous flow of cooling liquid is discharged through the longitudinal opening in the bur for discharge at the outer end thereof into the preparation formed in a tooth by said handpiece and bur at the innerface between the tooth substance and the bur where heat is generated under normal operations and laboratory measurements have disclosed that a bur when rotating at relatively high speed develops 5.88 BTU/min., which must be removed to prevent heat buildup. To evaluate the cooling effect of the invention, a dental drilling analyzer was developed to simulate and maintain reproducible tooth drilling conditions by so-called hollow dental burs through which cooling liquid is discharged.

DRILLING CONDITIONS:

Bur speed: 170,000 rpm
Bur torque: 0.001655 foot lbs.
Bur tooth interface temperature without water after a thirty second running time: 480° F.
Bur tooth interface temperature: Continuous 86° F. using a flow rate of 1 CC/min. of 68° F. cooling water.

From these data it shows that the method of utilizing cooling liquid in the present invention definitely prevents heat buildup in the operation of a dental bur. It reduces the water volume 16 times over the state of the art cooling methods and this improvement affords better operating visibility and higher drilling rates without pain to the patient and fear of tooth damage by the dentist.

Because of the reduction of the amount of cooling liquid which is employed, flooding of the operating site is reduced, or eliminated, because the small amount of cooling water leaving the tip of the bur is vaporized by the centrifugal force thereof, and does not appear as liquid water in the highly turbulent area around the cutting bur, thus producing a substantially dry operating area with excellent visibility for the dentist and provides a major improvement over the present state of the art with respect to cooling methods for a dental bur.

The control mechanism, which is described in detail hereinafter, allows the uninterrupted metered flow of cooling liquid, such as water, from the control cabinet through a rotary liquid seal in the handpiece and then to and through the longitudinal opening through the bur and out the tip end of the bur. As might be expected, the rotary seal development employs relatively new technology which affords a substantially leak-proof operation at speeds exceeding 400,000 rpm, with essentially zero drag in a space less than 0.340 inch diameter and 0.050 inch deep. The seal consists essentially of a rotary face, formed on the inward end of the bur, and a mating static face in the form of a flexible diaphragm with a 0.015 inch diameter hole in its center.

Some of the materials which are suitable for the elements of the seal comprise, in the bur: tool steel, 304 stainless steel, 430 stainless steel, tungsten carbide and other suitable materials that can be chrome plated at the seal end.

In the diaphragm: 0.055 inch thick Mylar, 0.005 inch thick Nylon, 0.010 inch thick ceramic and 0.005 inch thick Beryllium Copper. The selection of the materials depends essentially on the operating speed and the minerals present in the cooling liquid, such as water.

Figure 2:
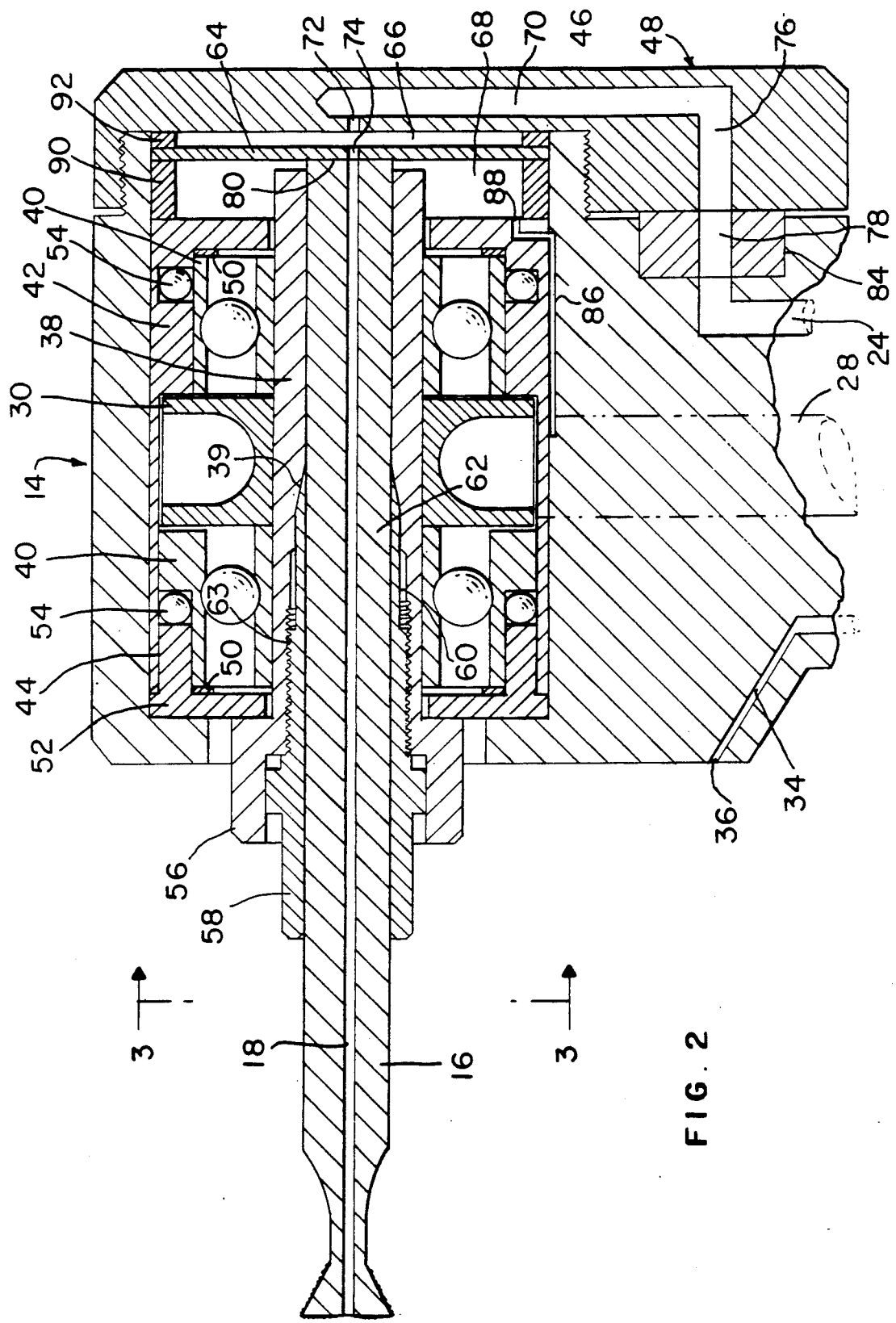
FIG. 2 is a fragmentary, cross-sectional view taken axially through the head of the handpiece and a portion of the handle secured thereto and illustrating details of the interior of the head and especially the manner in which several kinds of liquid are conducted through the head for cooling, as well as flushing purposes, and also showing passages for air to drive the turbine, as well as functioning in relation to a rotary liquid transmission coupling comprising a principal feature of the present invention.

Referring now particularly to FIG. 1 and FIG. 2 of the drawings, there is illustrated a dental handpiece 10, which includes a handle 12 and a head 14, the axis of which is transverse to the handle. Extending from the lower end of the head 14 is a dental bur 16 through which a longitudinal passage 18 extends between opposite ends thereof, as best shown in FIG. 2. As shown in FIG. 1, the tip end of the bur has cutting means which are shown in an exemplary cavity 20 in a tooth 22 in which the cavity is being shaped to receive a filling. The tooth 22 and cavity 20 are merely exemplary, as well as the bur 16.

The handle 12 contains a number of longitudinal passages which are shown in phantom in FIG. 1, these comprising a passage 24, through which cooling liquid is furnished for discharge from the longitudinal passage 18 of the bur. Also, the outermost end of the passage 26, shown in FIG. 1, is exemplary of exhaust means for driving air for the turbine which rotates within the head 14, as shown in FIG. 2. A passage 28 is the means by which driving air, under pressure, is delivered to the head of the handpiece to operate the turbine 30, which is shown in detail in FIG. 2. Lastly, still another passage 32 receives flushing liquid at its outer end and directs the same through an interior angular passage 34, see FIG. 1, through which flushing liquid is discharged from nozzle opening 36 toward the outer end of the bur 16 for purposes of flushing debris resulting from the drilling operation of the bur and this also affords limited cooling of the tooth but for reasons described hereinafter, such cooling is extremely limited and in accordance with the present invention, the principal cooling of the drilling operation is afforded by the longitudinal passage 18 within the bur 16.

The turbine 30 is mounted by a press fit or otherwise upon a tubular shaft 38 upon which the inner races of a pair of antifriction bearings 40 are mounted respectively on opposite sides of the turbine 30. The outer races of the bearings are mounted within a tubular shell 42, which comprises a housing comprising a cartridge within which the bearings and turbine are positioned for movement as a unit within a bore 44, see FIG. 2, of uniform diameter within the head 14. Especially from FIG. 2, it will be seen that the head 14 is somewhat cup-shaped and has an open upper end 46 which is closed by a threaded eccentric closure cap 48. Preload washers 50 abut the outer ends of the outer races of the bearings 40 which respectively abut the inner end of the tubular shell 42 and a closure member 52 for said shell, all of which are shown best in FIG. 2. O-rings 54 also aid in positioning the outer races of the bearings with respect to the tubular shell 42.

The tubular shaft 38, at its outer end, has an enlarged outer portion 56 which is interiorly threaded to receive a tightening nut 58 which is different from that shown in applicant's prior patent and has a thin longitudinally segmented compressible tapered extension 60 on its exterior end that engages a mating tapered bore 39 in the turbine shaft 38 and receives the shank of bur 16. The compressible extension 60 receives a substantial length of the shank 62 of bur 16 and when the tightening nut 58 is tightened by the action of intermediate threads 61 with interior threads 63 in turbine shaft 38, the shaft of the bur is securely clamped to the turbine shaft 38, whereby no relative rotation exists between the bur and the shaft.

One of the outstanding improvements afforded the present invention comprises a rotary liquid transmission, the primary elements of which comprise a flexible diaphragm. The principal preferred materials from which the diaphragm is made are set forth above. The diaphragm 64 is mounted intermediately between a relatively flat space 66 in the inner end of the head 14 and annular space 68 into which the superpolished and absolutely flat innermost end of the shaft 38 extends, as clearly shown in FIG. 2. The cap 48 also includes a radial passage 70, which is plugged at the outer end thereof and the inner end extends past the axis of the head and a central opening 72 of small diameter forms communication between passage 70 and space 66 for the passage of cooling liquid to space 66. Diaphragm 64 also has a small central opening 74, which is coaxial with opening 72.

Cooling liquid is furnished to radial passage 70 by means of connecting passages 76, 78, passage 78 actually comprising the inner end of passage 24 by which cooling liquid is furnished to the head 14. Since the eccentric cap 48 is threaded onto head 14, a flexible leak-proof cooling fluid seal must be provided to couple the passages 78 and 76 in the space between cap 48 and head 14. This is accomplished by a flexible "VITRON" ring 84, recessed in the head 14, and extending to sealing contact with cap 48 when the cap 48 is indexed to its final tight position.

The rotary liquid transmission coupling comprises the inner end 80 of rotary bur 16 which preferably is formed from any selection of tool steel 308, 430 stainless steel, Tungsten carbide and other suitable materials that can be chrome plated at the seal end. All of these have good wear and sealing characteristics, especially when used in contact with the diaphragm 64 when formed from self-lubricating plastic, such as Nylon or Mylar. The bur 16 also has a central longitudinal passage 18 extending entirely therethrough which is coaxial with openings 72 and 74 and serves to communicate with the longitudinal passage 18 in the bur 16.

For the most effective sealing between the inner end 80 of bur 16 and diaphragm 60, it is essential that the end 80 be superpolished and optically flat. The term superpolished means that there must be no roughness in excess of 0.001 micro inch. The material from which the bur is made must be corrosion-resistant to the cooling liquid. The bur must also be dynamically balanced on the central axis so that there is no vibration when rotating, especially at high speeds, and the bur must meet critical high speed cutting tool safety standards. From the foregoing, it will be seen that the surface 80 is precise and insures smooth movement with the stationary innermost surface of the flexible diaphragm 64.

The operation of the rotary liquid coupling also is dependent upon the delivery of a limited amount of the driving air from passage 28 in the handle 12 of the handpiece to a bypass conduit 86 of small size, which exits at 88 into the annular space 68 for the following purpose:

The operation of the rotary liquid transmission coupling is as follows: Back pressure is effected by cooling liquid within the flat space 66, as received from radial passage 70, through opening 72 and is exerted against a right-hand surface of diaphragm 64, as viewed in FIG. 2, while air under controlled pressure is furnished to annual space 68 and exerts pressure against the surface of the diaphragm next to space 68. The air and liquid pressures preferably are regulated so as to exert substantially equal pressure against opposite surfaces of the diaphragm 64 and thereby maintain the inner superpolished end 80 of the bur 16 in close contact with the adjacent surface of the diaphragm 64. This is especially desirable upon start-up of the turbine so that frictional contact will not cause overheating between the relative static and rotating surfaces of the diaphragm and inner end 80 of the bur 16, and when steady operation of the turbine occurs at high speeds, no appreciable friction will be generated between the engaging surfaces and the temperature of the cooling liquid likewise is present to effect cooling of the two relatively movable surfaces.

The diaphragm 64 is mounted between suitable annular gaskets 90 and 92, which, for example, may readily be formed from silicone rubber and thereby secure the edges of the diaphragm in sealed manner within the head of the handpiece.

The bur shank is securely fastened to the rotary shaft 38 by the compression of the compressible extension 60 of tightening nut 58 which firmly engages the shank 62 of the bur by tightening the nut 58 which is square on its outer end. The outer end of the turbine shaft 56 is also square to accept the bur-changing tool. The bur-changing tool is designed to permit one hand operation. One wrench of the tool engages shaft nut 56 and holds it stationary, while another manually-rotatable wrench engages the bur chuck nut 58 for opening or closing the chuck around the bur.

In operating the handpiece of the present invention, it has been found that when using the bur to drill or cut substances, such as bone and non-crystalline tooth material, there is a tendency for the resulting debris to clog at least the outer end of the longitudinal passage or bore in the bur. To tend to explain this phenomenon, the following is provided as an explanation, using a specific set of dimensions, without restriction thereto, which otherwise have been found to provide a satisfactory bur having desired cooling characteristics when operating upon certain test materials, such as crab claws, glass, oyster and conk shells.

The diameter of the bur passage or bore is 0.010 inch which has a cross-section area of 0.0000785 square inch. The coolant pressure at the upper end of the bur is 3 lbs. per square inch. This pressure produces a force across the 0.0000785 square inch area of the debris plug of $0.0000785 \times 3 = 0.0002355$ pounds, which is not capable of blowing the plug out. Laboratory testing has found that pluggage caused by tooth debris required a ram force of 0.525 pounds on a 0.008 inch diameter steel cleaning wire to remove the plug. To develop a hydraulic force capable of removing this plug, the force would be $0.525/0.0000785 = 6,687$ lbs.

This problem has been solved by providing a self-cleaning element inside the bur that prevents the build-up of debris materials that could cause pluggage.

Referring to FIGS. 13-15, the anti-clogging device comprises a clockwise wound flat coiled spring 202, preferably formed from hard-drawn stainless steel wire, one diameter of such wire that has been found operable is 0.006 inch for operation of a straight section of said spring wire within the passage or bore 18 of the bur which has a diameter of 0.010 inch.

The flat coiled spring 202 has one end 200 which is sharp and the opposite end extends inward strut-like toward the center of said coil 202 and then is bent sharply at a right-angle 203 to the plane of said flat coil 202, as shown in FIGS. 14 and 15, to provide an integral straight portion or section 205 which extends through the elongated opening 18 in the bur 16, as best shown in FIG. 13. The overall configuration of the spring portions 202 and 205 somewhat resembles an umbrella with a handle. The coil portion 202 also is capable of exerting limited axial pressure upon the straight portion 205 when mounted within the head and bur of the handpiece.

The space between the inner surface of the passage or bore 18 and the outer surface of the straight wire section 105 of the anti-clogging device disposed within the passage 16 is the conduit or passage for the coolant flow through the bur.

The rotation of the bur is clockwise, and the fluid friction between the bur and the wire tends to turn the wire clockwise. This causes the sharp end 200 of the wire spring 202 to frictionally engage or dig into the cap 48, similar to the action of a right-hand drill, and prevents rotation of the coil 202 of the spring. This provides a highly turbulent situation inside the bur between the bur bore wall and the straight wire 205, whereby any build-up of debris on the inner wall is instantly wiped away by the straight section 205 of the wire device and is swept out by the outward flowing coolant fluid. Laboratory testing has shown that this anti-clogging device is completely effective in preventing pluggage of the bur bore on all materials tested, such as wood, Nylon, acrylics, teeth, bone, steel-silver amalgams, brass, tungsten, carbide, aluminum, cast iron, silver, gold and animal tissue.

In order to improve coolant flow in extreme drilling conditions, cross-sections of the wire of the device other than round can be used to increase the cross-section area of the fluid passage between the bur bore and the wire section 205 without reducing the cleaning action of the invention. These wire cross-sections consist of "X", "Y", "+", "D" and triangular, for example.

The straight section 205 of the wire device normally extends about 1/32 inch past the outer end of the bur tip. When the bur contacts a tooth area, the straight section 205 of the wire device telescopes upwardly inside the bore. When the bur is withdrawn from the tooth surface, the wire tip 204 is projected to the extended position by the downward force of the compression configuration of the spring coil 202 attached to the upper end of the straight section 205 of the device. This action also helps removal of any material that may have pushed the cleaning wire upward during the drilling operation. It will thus be seen that the anti-clogging device shown in FIGS. 13-15 operates to prevent clogging of the bore or passage 18 in bur 16.

It will be understood that the aforementioned anti-clogging device has a coiled portion 202 normally installed in the flat space 66 between diaphragm 64 and the closure nut 48 for the head 14, and that the straight section 205 of the device, when the bur is removed from the tubular shaft 38 of the turbine, will project a substantial distance beyond the outer end of tightening nut 58. In view of the fact that the longitudinal passage or bore 18 in the bur 16 is only of the order of about 0.010 inch, when a bur is being repositioned in operative relation within the bore of the tubular shaft 38, it has been found desirable to provide in the flat end surface 80 of the bur 16, a preferably conical entry surface 206 coaxial with passage 18 of bur 16 into which the outer end 204 of the straight section 205 of the anti-clogging device initially is easily inserted and then the straight section 205 is slid into the longitudinal passage 18 of bur 16 for the full length thereof. Finally, the end 204 of section 205 will project a short distance beyond the outer end of the bur 16, as shown in FIG. 13 and described above.

Preferably, the surface of the end 80 of bur 16 which is occupied by the outer end of conical entry surface 206 comprises at least one-third of the total surface of said end 80. The remaining portion of the surface 80 is superpolished and absolutely flat, as described above.

CONTROL SYSTEM FOR AIR AND LIQUIDS

Figure 12:
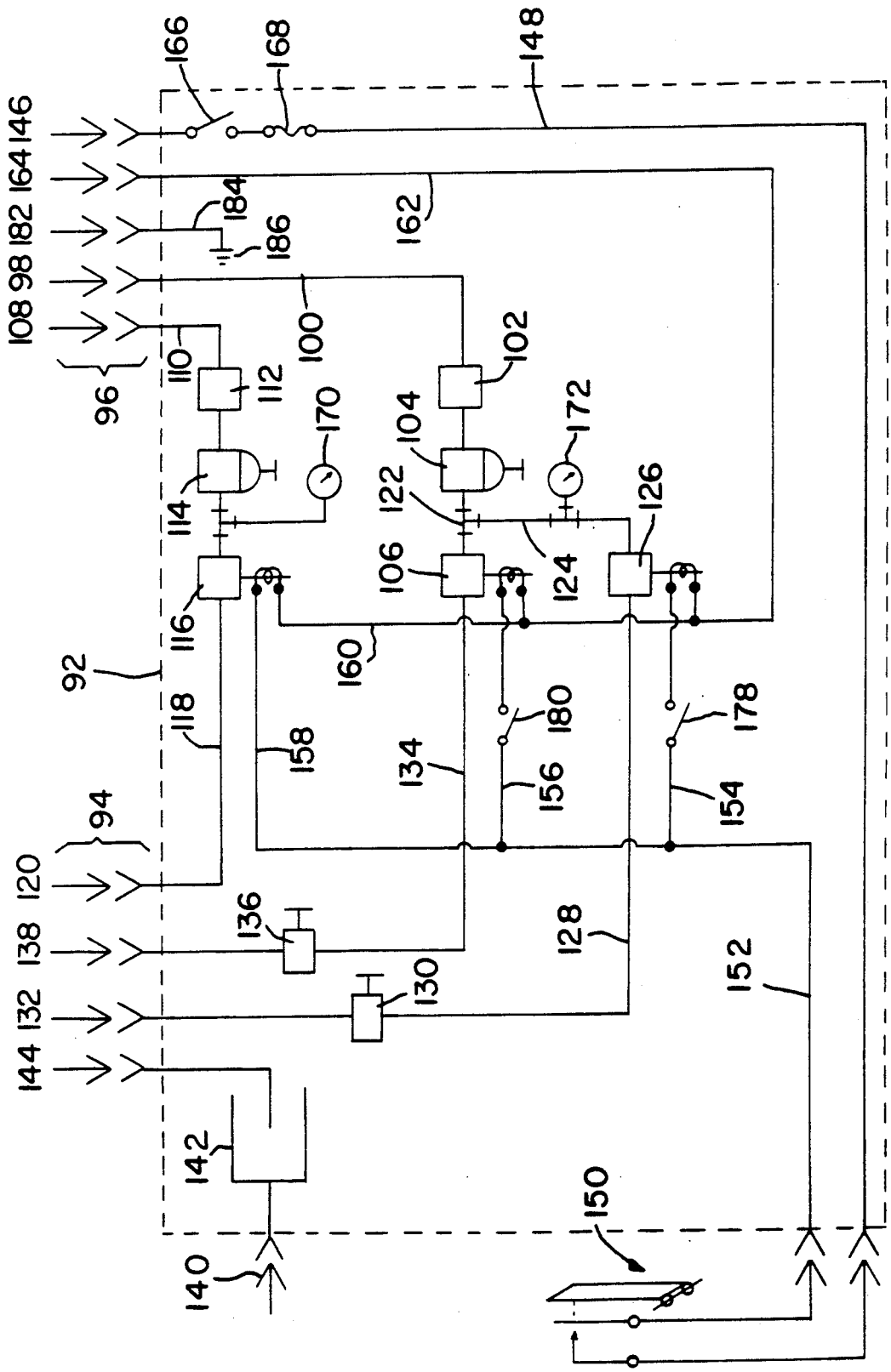
FIG. 12 is a diagrammatic illustration of control mechanism by which several types of liquid under controlled pressures, as well as air under controlled pressure, are delivered to the head of the handpiece.

The control mechanism by which driving air is applied to the turbine in the head of the handpiece and cooling liquid, as well as flushing liquid, are regulated as to volume and pressure for delivery to the head of the handpiece, is best shown schematically and diagrammatically in FIG. 4, it being understood the entire control unit is mounted in a small cabinet 92, illustrated by dotted lines in FIG. 12. The plug and socket units 94 and 96 are illustrated diagrammatically by spaced V's, and it will be understood that various air and liquid conducting tubes, as well as electric circuits, will be contained within cables, not shown, as currently used in many types of dental equipment at present. For example, the plug 98 is connected to a source of cooling liquid and passes through conduit 100 to a filter 102, a liquid pressure regulator 104 and then to a liquid control valve 106, which preferably is of the electric solenoid type. Compressed air plug 108 is connected to a suitable source of compressed air and conduit 110 conducts the air to an air filter 112, an air pressure regulator 114 and an air flow control solenoid valve 116. From the valve 116, conduit 118 communicates with plug 120, which connects conduit 118 with plug 120 to which driving air conduit 28 is connected.

Liquid pressure regulator 104 and liquid control valve 106 are connected by conduit 122 to which a bypass conduit 124 is connected to convey flushing water to an electric solenoid valve 126 and from which line 128 extends to water volume metering valve 130, which is manually-settable and communicates with plug 132 that is interconnected to passage 32 in the handle 12 of the handpiece, by which flushing liquid is delivered to nozzle 36. Solenoid control valve 106 for cooling liquid communicates with line 134 and manually-operable water volume metering valve 136, and is connected to plug 138, which is connected to conduit 24 in the handle of the handpiece for the delivery of cooling liquid to the bur 16.

Exhaust air from the turbine, after driving the same, discharges through passage 26 in the handle of the handpiece and connects to plug 144, shown in FIG. 12, for discharge of the exhausting air to an air-water separator 142, which is connected to outlet plug 140, as seen in FIG. 12.

The electrical system, which essentially controls and operates the electric solenoid valves 106, 116 and 126, comprises a plug 146, which is connected to a suitable source of current. It is connected to line 148, which extends to one pole of a foot-actuated switch 150 and the opposite pole of the switch is connected by line 152 to branch lines 154, 156 and 158, which respectively are connected to the solenoids of solenoid valves 106, 116 and 126. The opposite ends of the coils of the solenoids are connected respectively to a common line 160, which is connected to a neutral line 162, which, in turn, is connected to plug 164. Returning to line 148, it will be seen that it includes a main switch 166 and a fuse 168. Also, an air-pressure gauge 170 is connected to the line between air-pressure regulator 114 and air flow control solenoid valve 116 for ready observation. Similarly, water pressure gauge 172 is connected in bypass conduit 124 and suitably visible to an operator of the system.

From the foregoing it will be seen that upon closing the foot switch 150, air pressure rises before the liquid pressure causes the diaphragm 64 to become slightly spaced from the rotary seal 80, and thereby allows a limited amount of air to flow through the bur around the open seal. This prevents dry operation of the seal which, if permitted, could damage it. Air also passes through the opening 74 in the seal and prevents liquid from passing through the open seal. When the liquid pressure equals the air pressure on the opposite sides of the diaphragm, the seal effected by the diaphragm closes or partly closes, allowing a small amount of air to continue to pass to the lower pressure inside the longitudinal opening of the bur. Where it exits at the bur tip, as a mixture of water and air, the amount of air leaking through into the bur reduces the seal friction drag and completely eliminates liquid getting into the ball bearings of the turbine when the drill is running. When the driving air for the turbine is shut off, the seal completely closes because of pressure loss on the rotary mating side of the diaphragm. A conventional cooling liquid jet spray or flush system is provided to allow the use of standard solid shank burs in the handpiece, if desired.

One of the useful aspects of the present invention also resides in the fact that branch lines 154 and 156 respectively include manually-operable control switches 178 and 180, which are connected in the circuits to the electric solenoid valve 126 and the liquid control valve 106, whereby three modes of cooling are possible. Mode 1 comprises directing cooling liquid to the bur only through plug 138, as controlled by the water volume-metering valve 136; Mode 2 comprises supplying cooling liquid to the bur and also flushing liquid to nozzle 36; and Mode 3 comprises directing cooling water only to nozzle 36, the operation of the manual switches 178 and 180 being the means by which such modes are established or discontinued.

It also will be seen that by the various control means for pressure and volume, a delicate balance is established in the pressures exerted against the diaphragm 64 and, when the control means are properly operated, effective sealing is established between the rotatable seal member 80 and the adjacent surface of the diaphragm 64 without undue wear occurring.

The cabinet 92 is made of any suitable material, such as plastic, sheet metal, or otherwise. For purposes of grounding the cabinet, especially if made of metal, as well as all the circuitry therein, a plug 182 is provided, as shown in the upper right-hand corner of FIG. 12, in exemplary manner, and a conductor 184, which is connected to the socket for plug 182, is connected to a ground 186.

The foregoing description illustrates preferred embodiments of the invention. However, concepts employed may, based on such description, be employed in other embodiments without departing from the scope of the invention. Accordingly, the following claims are intended to protect the invention broadly, as well as in the specific forms shown herein.

I claim:

1. An air turbine type dental handpiece comprising in combination,
   a. a handle having passages therein attachable respectively to sources of air and cooling liquid under controllable pressure,
   b. a hollow head connected to one end of said handle and having additional passages for air and cooling liquid respectively connected to said passages in said handle,
   c. a turbine rotatably mounted in said head upon bearings at opposite ends of a tubular shaft projecting respectively in opposite directions through said turbine and bearings and said air passage in said head directing air under pressure to said turbine to drive it,
   d. a dental bur having a longitudinal opening extending entirely therethrough for the passage of cooling liquid therethrough and insertable operatively and axially within said shaft, the cutting end of said bur projecting beyond one end of said shaft and the opposite end of said bur projecting a limited distance beyond the opposite end of said shaft and terminating adjacent the upper interior portion of said head, and
   e. a rotary liquid seal member mounted within the upper portion of said head between the innermost end of said bur shank and the passage in said head for transmission of cooling liquid to the outer end of said bur and directly engaged rotatably by said innermost end of said bur shank and operative to seal said passage for cooling liquid against escape of liquid to said bearings and turbine, said innermost end of the bur shank being optically flat and highly polished due to having roughness at least less than 0.001 micro inch.

2. The dental handpiece according to claim 1 in which said rotary liquid seal member comprises a flexible diaphragm sealed at the edges thereof in the upper end portion of said head, said cooling liquid passage in said head being arranged to discharge liquid against one face of said diaphragm and said diaphragm having a small substantially central opening coaxial with the upper end of said bur shank, and said optically flat upper end of said bur shank providing a rotary seal rotatable directly against the portion of the other face of said diaphragm which is coaxial with the opening therein, whereby cooling liquid directly under pressure against said one face of said diaphragm biases the same against said highly polished end on said bur shank and permits discharge of cooling liquid to and through the axial passage of said bur to the discharge end thereof.

3. The dental handpiece according to claim 2 in which said diaphragm is formed from thin self-lubricating plastic sheet material and rotary seal comprises the upper end of said bur shank being optically flat and superpolished for rotatable engagement directly against said other face of said diaphragm.

4. The dental handpiece according to claim 1 in which said bur is corrosion-resistant to cooling liquids.

5. A dental bur having cutting means on one end of an elongated shank of uniform outer diameter and said shank having a longitudinal opening therein extending entirely therethrough from end to end for the passage of cooling liquid therethrough to discharge at the tip of the cutting end of said bur, and the opposite end of said bur having an optically flat surface which is highly polished to comprise part of a liquid rotary seal for controlling the passage of cooling liquid through said longitudinal opening therein, said optically flat highly polished surface having a roughness less than 0.001 micro inch.

6. A dental handpiece comprising in combination,
   a. a handle having at least one passage therein connectable at one end to a source of cooling liquid under pressure,
   b. a hollow head connected to the other end of said handle,
   c. a rotatable member supported upon a pair of axially-spaced bearings within said head,
   d. said rotatable member having a longitudinal opening extending therethrough to receive a
   e. dental bur which also has a longitudinal opening extending therethrough between the opposite ends of said bur and adapted to receive cooling liquid from said handle,
   f. a rotary liquid seal unit mounted within the upper portion of said head and operable to receive cooling liquid from said passage in said handle and direct it to the inner end of said rotatable member for discharge to the innermost end of the passage in said bur for discharge of said cooling liquid through the opposite end of said bur,
   g. said opposite end of said bur extending through and beyond an opening in the lower portion of said head,
   h. an anti-clogging device having an elongated portion of less diameter than the diameter of said longitudinal opening in said bur, said elongated portion extending through said longitudinal opening in said bur and the longitudinal space between said elongated portion of said device and the inner wall of said longitudinal opening in said bur comprising a discharge passage for said cooling liquid operable to flush from said passage any debris resulting from the cutting action of said bur while also cooling the surface of the dental preparation being contacted by said bur, and
   i. means in said head operable to rotate said rotatable member.

7. The dental handpiece according to claim 6 wherein said anti-clogging device comprising an elongated straight wire portion of said device extending within the elongated opening is said bur for the full length thereof.

8. The dental handpiece according to claim 7 wherein the outer end of said straight wire portion of said device normally extends a very short distance beyond the outer end of said bur for contact with a dental surface being formed by said bur.

9. The dental handpiece according to claim 6 wherein said rotary liquid seal unit in the upper portion of said head comprises a flat space between a cap for the upper end of said head and a flexible diaphragm engageable rotatably by the inner end of said bur when cooling liquid is directed from said handle to the upper end of said head and said diaphragm having an opening centrally thereof and aligned with said longitudinal opening in said bur, and said anti-clogging device comprising a planar coil of spring wire of limited convolutions mounted within said flat space in said head and one end of said spring coil being sharp for frictional engagement with said cap and the opposite end of said spring comprising a straight portion disposable within the passage in said bur and is connected to said coil by a short radial strut section.

10. The dental handpiece according to claim 9 in which the outer end of said straight portion of said anti-clogging device normally is urged by said coiled spring portion of said device to extend beyond the outer end of said bur for direct contact with the surface of a tooth when being cut by said bur but is capable of retraction within the bore of said bur against the action of said coiled spring section of said device.

11. The dental handpiece according to claim 9 in which said coiled spring portion of said device is coiled in one direction and said means to drive said rotatable member to rotate said bur is designed to rotate said bur in the same direction, whereby friction induced by the fluid between the opening in the bur and the straight wire section of the device in said opening tends to turn the latter in said same direction and causes said sharp end of the coiled spring section of the device to frictionally engage the cap of the head to prevent rotation of the coiled spring section and thereby causes appreciable turbulence in the cooling liquid when passing through the bur which turbulence prevents any accumulation of debris within the bur as flushed by said cooling liquid.

12. The dental handpiece according to claim 6 in which said rotatable member in said head is a turbine and said handle is provided with an additional passage connectable with a source of fluid under pressure and the head has means to direct said fluid against the turbine to rotate it and the bur within a bore in the shaft of said turbine.

13. The dental handpiece according to claim 6 in which the inner end of said bur has a conical entry surface coaxial with the longitudinal passage therein and adapted to facilitate the insertion of said elongated portion of said anti-clogging device into the longitudinal opening in said bur when a bur is being mounted in the longitudinal opening of said rotatable member.

14. A dental bur having cutting means at one end of an elongated shank of uniform diameter and said shank having a longitudinal opening therein extending entirely therethrough from end to end for passage of cooling liquid therethrough to discharge it at the tip of the cutting end of said bur, and the opposite end of said bur having a flat surface provided with a central conical entry surface coaxial with said longitudinal opening and adapted to facilitate the insertion of the end of an elongated anti-clogging device therein when inserting said bur in operative position within the rotatable member of a dental handpiece.

* * * * *